US012667814B2

(12) United States Patent
Keinath et al.

(10) Patent No.: US 12,667,814 B2
(45) Date of Patent: Jun. 30, 2026

(54) PREPARATION OF AN AMINO-FUNCTIONAL POLYORGANOSILOXANE EMULSION

(71) Applicant: Dow Silicones Corporation, Midland, MI (US)

(72) Inventors: Mark Keinath, Midland, MI (US); Jennifer Reil, Midland, MI (US)

(73) Assignee: Dow Silicones Corporation, Midland, MI (US)

( * ) Notice: Subject to any disclaimer, the term of this patent is extended or adjusted under 35 U.S.C. 154(b) by 252 days.

(21) Appl. No.: 18/749,677

(22) Filed: Jun. 21, 2024

(65) Prior Publication Data

US 2024/0335800 A1 Oct. 10, 2024

Related U.S. Application Data

(63) Continuation-in-part of application No. PCT/US2023/063307, filed on Feb. 27, 2023.

(60) Provisional application No. 63/324,765, filed on Mar. 29, 2022.

(51) Int. Cl.

| | |
|---|---|
| ***B01F 23/41*** | (2022.01) |
| ***A61K 8/06*** | (2006.01) |
| ***A61K 8/898*** | (2006.01) |
| ***A61Q 5/12*** | (2006.01) |
| *B01F 101/21* | (2022.01) |

(52) U.S. Cl.

CPC ............ *B01F 23/4105* (2022.01); *A61K 8/06* (2013.01); *A61K 8/898* (2013.01); *A61Q 5/12* (2013.01); *B01F 2101/21* (2022.01); *B01F 2215/044* (2013.01); *B01F 2215/0468* (2013.01); *B01F 2215/0472* (2013.01)

(58) Field of Classification Search

None

See application file for complete search history.

(56) References Cited

U.S. PATENT DOCUMENTS

| | | | |
|---|---|---|---|
| 4,122,029 A | 10/1978 | Gee et al. | |
| 5,387,417 A | 2/1995 | Rentsch | |
| 5,811,487 A | 9/1998 | Schulz, Jr. et al. | |
| 6,083,854 A | 7/2000 | Bogdanski et al. | |
| 6,171,515 B1 | 1/2001 | Evans et al. | |
| 7,238,768 B2 | 7/2007 | Hupfield et al. | |
| 7,781,505 B2 | 8/2010 | Cook et al. | |
| 11,028,229 B2 | 6/2021 | Suthiwangcharoen et al. | |
| 11,028,233 B2 | 6/2021 | Suthiwangcharoen et al. | |
| 2004/0210074 A1 | 10/2004 | Hupfield et al. | |
| 2005/0255075 A1 | 11/2005 | Meder et al. | |
| 2007/0099007 A1 | 5/2007 | Benayoun et al. | |
| 2008/0242744 A1 | 10/2008 | Barnes et al. | |
| 2011/0059038 A1 * | 3/2011 | Gabelnick .............. | A61K 8/463 424/78.03 |
| 2018/0353396 A1 | 12/2018 | Paul et al. | |
| 2020/0325280 A1 | 10/2020 | Feng et al. | |
| 2022/0008320 A1 | 1/2022 | Liang et al. | |
| 2024/0130955 A1 | 4/2024 | Ando | |

FOREIGN PATENT DOCUMENTS

| | | |
|---|---|---|
| CN | 103497339 | 8/2015 |
| WO | 2013082096 | 6/2013 |
| WO | 2016123347 | 8/2016 |

OTHER PUBLICATIONS

Koretemeier, "Thickening Agents for Surfactants Systems", SOFW Journal, 2010, vol. 136, pp. 30-38.

Perazzo, "Phase inversion emulsification: Current understanding and applications", Advances in Colloidal and Interface Science 222, 2015, pp. 581-599.

* cited by examiner

*Primary Examiner* — Brian J Davis

(74) *Attorney, Agent, or Firm* — Catherine U. Brown

(57) ABSTRACT

A process is provided for preparing an aqueous emulsion of an amino-functional polyorganosiloxane. The process includes mixing A) an amino-functional polyorganosiloxane, B) a non-ionic surfactant, and C) water; and thereafter mixing in additional starting materials including additional water, D) a water soluble salt, E) a pH adjusting agent, and F) a preservative. A phase inversion occurs during the process, such that the resulting emulsion has A) the amino-functional polyorganosiloxane in the internal, discontinuous phase and C) the water in an external, continuous phase.

17 Claims, No Drawings

PREPARATION OF AN AMINO-FUNCTIONAL POLYORGANOSILOXANE EMULSION

CROSS REFERENCE TO RELATED APPLICATIONS

This application is a continuation in part of PCT Application No. PCT/US23/063307 filed on 27 Feb. 2023, currently pending, which was published under PCT Article 21 (2) in English, which claims the benefit of U.S. Provisional Patent Application Ser. No. 63/324,765 filed on 29 Mar. 2022 under 35 U.S.C. § 119 (e). PCT Application No. PCT/US23/063307 and U.S. Provisional Patent Application Ser. No. 63/324,765 are hereby incorporated by reference.

TECHNICAL FIELD

A process for preparing an emulsion of an amino-functional polyorganosiloxane is provided.

INTRODUCTION

Emulsions of amino-functional polyorganosiloxanes are widely used in hair care compositions to provide various aesthetic benefits. Various types of emulsions have been commercially developed to provide water-based products of such amino-functional polyorganosiloxanes for use as hair conditioning agents. One method to prepare emulsions of amino-functional polyorganosiloxanes involves emulsion polymerization techniques, where siloxane monomers are first emulsified, and then subsequently polymerized to a high molecular weight. Alternatively, mechanical emulsions may be prepared from pre-formed amino-functional polyorganosiloxanes.

PROBLEM TO BE SOLVED

Each of these methods can have issues with viscosity stability upon aging. Due to the hydrophilic nature of aminosiloxanes the polymer can migrate to the particle interface. Interactions between the particles can become significant enough to increase the bulk viscosity to a level where the material is paste like and will not readily flow from its container. Furthermore, the viscosity will drift with time as the material ages causing customer concerns as the observed viscosity is no longer consistent to the value listed on the certificate of analysis. The high viscosity has been historically mitigated by lowering the concentration of aminosiloxane. However, this has a detrimental cost at the manufacturing site, while being transported, and during customer use.

SUMMARY

A process where small quantities of certain salt compounds can counteract the undesirable high bulk viscosity while maintaining stability of the formulation throughout the shelf life of an aqueous emulsion. The process for preparing the aqueous emulsion of an amino-functional polyorganosiloxane comprises: 1) mixing starting materials comprising: A) an amino-functional polyorganosiloxane, B) a non-ionic surfactant, and C) water, thereby preparing a water-in-oil dispersion (having C) the water in an internal, discontinuous phase and A) the amino-functional polyorganosiloxane an external, continuous phase); and thereafter mixing additional starting materials comprising additional water, D) a water soluble salt, E) a pH adjusting agent, and F) a preservative. A phase inversion occurs such that the resulting emulsion has A) the amino-functional polyorganosiloxane in the internal, discontinuous phase and C) the water in an external, continuous phase.

DETAILED DESCRIPTION

A process is provided for preparing an aqueous emulsion of an amino-functional polyorganosiloxane. The process comprises mixing starting materials comprising A) an amino-functional polyorganosiloxane, B) a non-ionic surfactant, and C) water; and thereafter mixing additional starting materials comprising additional water, D) a water soluble salt, E) a pH adjusting agent, and F) a preservative. A phase inversion occurs during the process, such that the emulsion produced by the process has A) the amino-functional polyorganosiloxane in the internal, discontinuous phase and C) the water in an external, continuous phase.

The process for making the emulsion may comprise:

1) mixing starting materials comprising
   - 25 weight parts to 75 weight parts of A) an amino-functional polyorganosiloxane,
   - 2 weight parts to 10 weight parts of B) a non-ionic surfactant, and
   - 4 weight parts to 20 weight parts of C) water;
2) mixing, with the product of step 1), starting materials comprising
   - 0.02 weight part to 1 weight part of D) a salt, and
   - additional water; and
3) mixing starting materials comprising
   - E) a pH adjusting agent,
   - F) a preservative, and
   - optionally G) a freeze inhibitor.

In the process described above, step 1) is performed before steps 2) and 3). Steps 2) and may be performed in any order. Alternatively, steps 2) and 3) may be performed sequentially. Alternatively, steps 2) and 3) may be performed concurrently.

In the process described herein, step 1) may be performed at a temperature of 10° C.-70° C. (alternatively 25° C.), shear rates of 70-700 $s^{-1}$ (alternatively 180 $s^{-1}$), and a pressure of 100-760 torr (alternatively 200-500 torr). Alternatively, step 1) may be performed under vacuum, e.g. <760 torr, to minimize foam creation. Step 2) may be performed at a temperature 10° C.-70° C. (alternatively 25° C.), shear rates of 7-90 $s^{-1}$ (alternatively 45 $s^{-1}$), and a pressure of 100-760 torr (alternatively 200 torr). Step 3) may be performed at a temperature 10° C.-70° C. (alternatively 25° C.), shear rates of 7-90 $s^{-1}$ (alternatively 45 $s^{-1}$), and a pressure of 100-760 torr (alternatively 200 torr).

The process described above may optionally further comprise one or more additional steps selected from:

- adding additional water after step 1) and before step 2) and mixing;
- adding additional water during or after step 2) and before step 3) and mixing;
- adding additional water during or after step 3) and mixing.

Furthermore, one skilled in the art would recognize that starting materials E), F) and when present G) may be added concurrently, alternatively, they may be added in any order. The process may optionally further comprise a post-processing step after the emulsion has been prepared as described above. For example, the process may further comprise filtering the emulsion after step 3) and/or packaging of the after step 3).

The process may optionally further comprise: first mixing A) the amino-functional polyorganosiloxane and B) the non-ionic surfactant and thereafter adding C) the water and mixing in step 1). The amount of water added in step 1) depends on various factors including the shear device selected for performing step 1). For example, a change can mixer, a rotor-stator mixer, a sonolator, an extruder, such as a twin screw extruder, a colloid mill, a stirred tank, a conical screw, or a homogenizer may be used for mixing in step 1). The same or different equipment may be used for the other steps of the process described herein. The amount of water added in step 1) may be 4 weight parts to 20 weight parts, alternatively 5 weight parts to 18 weight parts, alternatively 5.5 weight parts to 16 weight parts, alternatively 6 weight parts to 14 weight parts, and alternatively 6.5 weight parts to 12 weight parts. Alternatively, the amount of water added in step 1) may be 4% to 20%, alternatively 8% based on combined weights of all starting materials in the emulsion.

Starting materials used in the process described herein include A) the amino-functional polyorganosiloxane, B) the non-ionic surfactant, C) the water, D) the water soluble salt, E) the pH adjusting agent, F) the preservative, and optionally G) the freeze inhibitor, which are introduced above and described in detail below.

A) Polyorganosiloxane

The amino-functional polyorganosiloxane comprises two or more siloxane units, which may be independently selected from M units of formula ($R_3SiO_{1/2}$), D units of formula ($R_2SiO_{2/2}$), T units of formula ($RSiO_{3/2}$), and Q units of formula ($SiO_{4/2}$), where each R is independently selected from an alkyl group and an amino-alkyl-functional group, with the proviso that at least one unit per molecule has an R which is the amino-alkyl-functional group. The amino-functional polyorganosiloxane further comprises a terminal unit of formula ($ZO_{1/2}$), where Z is selected from the group consisting of H and $R_1$, an alkyl group of 1 to 6 carbon atoms, described in further detail below. These siloxane units can be combined in various manners to form cyclic, linear, or branched structures. Suitable amino-functional polyorganosiloxanes are as disclosed, for example, in PCT Published Patent Application No. WO2013/082096.

Alternatively, the amino-functional polyorganosiloxane may be substantially linear or linear. The amino-functional polyorganosiloxane may comprise an amino-functional polydiorganosiloxane. Alternatively, the amino-functional polydiorganosiloxane may comprise a poly(dialkyl/alkyl, amino) siloxane of unit formula: $(R^1_2SiO_{2/2})_a(R^1R^2SiO_{2/2})_b(ZO_{1/2})_d(R^1_3SiO_{1/2})_e$, where each $R^1$ is an independently selected alkyl group of 1 to 6 carbon atoms; each $R_2$ is an independently selected amino-functional alkyl group; subscripts a, b, d, and e represent average number, per molecule, of each unit in the unit formula, subscript a is 1 to 5, subscript bis 1 to 1000; subscript d is 0, 1, or 2, alternatively 1 or 2; subscript e is 0, 1, or 2, alternatively 0 or 1; and a quantity (d+c)=2. Alternatively, subscript a may be 2 to 5, alternatively 2 to 4, and alternatively 1 to 4. Alternatively, subscript b may be 50 to 900, alternatively 100 to 800, alternatively 150 to 700, alternatively 200 to 600, alternatively 300 to 550, alternatively 350 to 550, and alternatively 400 to 500. Alternatively, a quantity (a+b) may have a value sufficient to give the poly(dialkyl/alkylamino) siloxane a viscosity of 3,000 to 8,000 centiPoise at 25° C. measured with Brookfield DV Viscometer using LV #4 at 30 rpm.

$R^1$ is an alkyl group of 1 to 6 carbon atoms and is exemplified by methyl, ethyl, propyl (including n-propyl and isopropyl), and butyl (including n-butyl, iso-butyl, sec-butyl, and tert-butyl). Alternatively, $R^1$ may be methyl or ethyl. Alternatively, each $R^1$ may be methyl.

$R^2$ is the amino-functional alkyl group. The aminofunctional alkyl group may have formula $ZHN—R^3—(ZNR^4)_c—$, where Z is as described above, $R^3$ is an alkylene group of 2 to 6 carbon atoms, $R^4$ is an alkylene group of 2 to 6 carbon atoms, and subscript c is 0 or 1. Examples of alkylene groups for $R^3$ and $R^4$ include of empirical formula $—C_rH_{2r}—$, where subscript r is 2 to 8. The alkylene group may be a linear alkylene, e.g., $—CH_2—CH_2—$, $—CH_2—CH_2—CH_2—$, $—CH_2—CH_2—CH_2—CH_2—$, or $—CH_2—CH_2—CH_2—CH_2—CH_2—CH_2—$, or a branched alkylene, e.g.,

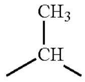,
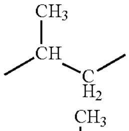,
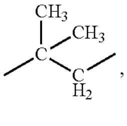, or
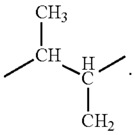.

Examples of amino-functional alkyl groups for $R^2$ include, but are not limited to, aminoethyl-, aminopropyl-, aminoisobutyl-, aminoethyl-aminopropyl-, and aminoethyl-aminoisobutyl-.

Amino-functional polyorganosiloxanes are known in the art, and many are commercially available. Representative commercial amino-functional organopolysiloxanes include XIAMETER™ OFX-8040 Fluid, XIAMETER™ OHX-8630 Fluid, XIAMETER™ OHX-8803 Fluid, DOWSIL™ AP-6087 Fluid, DOWSIL™ AP-8087 Fluid, and DOWSIL™ 2-8566 Amino Fluid, all of which are commercially available from Dow Silicones Corporation of Midland, Michigan, USA. Amino-functional polyorganosiloxanes may be made by known methods, such as those disclosed in U.S. Pat. No. 11,028,233 to Suthiwangcharoen, et al; U.S. Pat. No. 11,028,229 to Suthiwangcharoen, et al.; U.S. Pat. No. 7,781,505 to Cook, et al.; U.S. Patent Application Publication 2004/0210074; U.S. Pat. No. 7,238,768 to Hupfield, et al; U.S. Pat. No. 6,171,515 to Evans et al.; and U.S. Pat. No. 2,947,771 to Bailey.

In the emulsion prepared as described herein, one or more of the above amino-functional polyorganosiloxanes may be used as starting material A). The amount in the emulsion produced by the process may be 25 weight parts to 75 weight parts, alternatively 30 weight parts to 70 weight parts, alternatively 35 weight parts to 65 weight parts, alternatively 40 weight parts to 60 weight parts, alternatively 45 weight parts to 55 weight parts, and alternatively 50 weight parts. Alternatively, the amount of A) the amino-functional polyorganosiloxane may be 35 weight parts to 75 weight parts, alternatively 40 weight parts to 70 weight parts, alternatively 45 weight parts to 65 weight parts, alternatively 50 weight parts to 75 weight parts, and alternatively 50 weight parts to 65 weight parts. Without wishing to be bound by theory, it is thought that the process for preparing the emulsion described herein allows for a relatively high loading (e.g., at least 35%, alternatively at least 50%, of the emulsion produced is A) the amino-functional polyorganosiloxane).

B) Non-Ionic Surfactant

Starting material B) in the emulsion prepared herein is a non-ionic surfactant. The emulsion may be free of cationic surfactant. Without wishing to be bound by theory, it is thought that the presence of a cationic surfactant may contribute to the undesirable formation of cyclic siloxanes (e.g., octamethylcyclotetrasiloxane, decamethylcyclopentasiloxane, and/or dodecamethylcyclohexasiloxane) when the emulsion is stored for a period of time before use.

Some suitable non-ionic surfactants which can be used herein include polyoxyethylene alkyl ethers (such as, lauryl, cetyl, stearyl or octyl), polyoxyethylene alkyl phenol ethers, alkylglycosides, polyoxyethylene fatty acid esters, sorbitan fatty acid esters, polyoxyethylene sorbitan fatty acid esters, polyoxyethylene sorbitan monooleates, polyoxyethylene alkyl esters, polyoxyethylene sorbitan alkyl esters, polyethylene glycol (such as polyethylene glycol having 23 ethylene-oxide units), polypropylene glycol, diethylene glycol, ethoxylated trimethylnonanols, tristyrylphenol ethers (TSP's), distyryl phenol ethers (DSP's), and polyoxyalkylene glycol modified polysiloxane surfactants.

Non-ionic surfactants which are commercially available include compositions such as 2,6,8-trimethyl-4-nonyloxy polyethylene oxyethanols (6EO) and (10EO) sold under the names TERGITOL™ TMN-6 and TERGITOL™ TMN-10; $C_{11-15}$ secondary alkyl polyoxyethylene ethers (e.g., $C_{11-15}$ secondary alcohol ethoxylates 7EO, 9EO, and 15EO sold under the names TERGITOL™ 15-S-7, TERGITOL™ 15-S-9, and TERGITOL™ 15-S-15, which has HL value 15.4), other $C_{11-15}$ secondary alcohol ethoxylates sold under the tradenames ECOSURF™ EH-40 and TERGITOL™ 15-S-12, TERGITOL™ 15-S-30, and TERGITOL™ 15-S-40, by The Dow Chemical Company, of Midland, Michigan, USA; octylphenyl polyoxyethylene (40) ether sold under the name TRITON™ X405 by the Dow Chemical Company; nonylphenyl polyoxyethylene (10) ether sold under the name MAKON™ 10 by the Stepan Company; ethoxylated alcohols sold under the name Trycol 5953 by Henkel Corp./Emery Group, of Cincinnati, Ohio, USA; ethoxylated alcohols sold under the name BRIJ™ L23 (with HLB value of 16.9) and BRIJ™ L4 (with HLB value of 9.7) by Croda Inc. of Edison, New Jersey, USA, polyoxyethylene 23 lauryl ether (Laureth-23) sold commercially under the trademark BRIJ™ 23 by ICI Surfactants, Wilmington, Delaware; and RENEX™ 30, a polyoxyethylene ether alcohol sold by ICI Surfactants, Wilmington, Delaware, USA; alkyl-oxo alcohol polyglycol ethers such as GENAPOL™ UD 050 (with HLB value of 11.4), and GENAPOL™ UD110 (with HLB value of 14.4), alkyl polyethylene glycol ether based on C10-Guerbet alcohol and ethylene oxide such as LUTENSOL™ XP 79, and alkyl polyglycosides, such as those sold under the trade name Glucopon™ by BASF, and alkyl glucosides such as decyl glucoside, lauryl glucoside, and coco-glucoside, which are sold under the trade name EcoSense™ by The Dow Chemical Company of Midland, Michigan, USA. Other commercially available non-ionic surfactants include TERGITOL™ 15-S-5, also from The Dow Chemical Company, which has an HLB value of 10.5; Lutensol XP 50 with an HLB value of 10, and Lutensol XP 140 with an HLB value of 16.

Suitable non-ionic surfactants also include poly(oxyethylene)-poly(oxypropylene)-poly(oxyethylene) tri-block copolymers. Poly(oxyethylene)-poly(oxypropylene)-poly (oxyethylene) tri-block copolymers are also commonly known as Poloxamers. They are non-ionic triblock copolymers composed of a central hydrophobic chain of polyoxypropylene (poly(propylene oxide)) flanked by two hydrophilic chains of polyoxyethylene (poly(ethylene oxide)). Poly(oxyethylene)-poly(oxypropylene)-poly(oxyethylene) tri-block copolymers are commercially available from BASF of Florham Park, New Jersey, USA, and are sold under the tradename PLURONIC™, such as PLURONIC™ L61, L62, L64, L81, P84.

The non-ionic surfactant may also be a silicone polyether (SPE). The silicone polyether as a surfactant may have a rake type structure wherein the polyoxyethylene or polyoxyethylene-polyoxypropylene copolymeric units are grafted onto the siloxane backbone, or the SPE can have an ABA block copolymeric structure wherein A represents the polyether portion and B the siloxane portion of an ABA structure. Alternatively, the SPE may have a resinous structure, such as a polyorganosilicate resin having polyether groups bonded to silicon atoms therein. Suitable SPE's include DOWSIL™ OFX-5329 Fluid from Dow Silicones Corporation of Midland, Michigan, USA. Alternatively, the non-ionic surfactant may be selected from polyoxyalkylene-substituted silicones, silicone alkanolamides, silicone esters and silicone glycosides. Such silicone-based surfactants may be used to form such aqueous emulsions and are known in the art, and have been described, for example, in U.S. Pat. No. 4,122,029 to Gee et al., U.S. Pat. No. 5,387,417 to Rentsch, and U.S. Pat. No. 5,811,487 to Schulz et al. Other silicone polyether surfactants are known in the art and are also commercially available, e.g., DOWSIL™ 502W and DOWSIL™ 67 Additive are commercially available from Dow Silicones Corporation of Midland, Michigan, USA.

Alternatively, the non-ionic surfactant may comprise a polyvinyl alcohol compound. Polyvinyl alcohol compounds are known in the art and are disclosed, for example in U.S. Patent Application Publication 2007/0099007 at paragraphs and [0173]. Polyvinyl alcohol compounds may be made by saponification of polyvinylacetate, so up to 15% of polyvinylacetate may remain in the polyvinyl alcohol compound used herein. Alternatively, the polyvinyl alcohol compound may be 88% to 92% polyvinyl alcohol (with the balance being 12% to 8% polyvinylacetate). The polyvinyl alcohol compound may have a minimum viscosity of 5 cP at 4% aqueous solution at 20° C.

In the emulsion prepared as described herein, one or more of the above non-ionic surfactants may be used. The exact amount of the non-ionic surfactant in the emulsion depends on various factors including the amino-functional polyorganosiloxane selected, the selection of non-ionic surfactant, and the amount of water and other components of the emulsion, however, the amount of non-ionic surfactant may be 2 weight parts to 10 weight parts, alternatively 2.5 weight parts to 8 weight parts, alternatively 3 weight parts to 6 weight parts, alternatively 3.5 weight parts to 5 weight parts, alternatively 4 weight parts to 5 weight parts, alternatively 4 weight parts to 4.5 weight parts, and alternatively 4.3 weight parts.

C) Water

The water is not generally limited, and may be utilized neat (i.e., absent any carrier vehicles/solvents), and/or pure (i.e., free from or substantially free from minerals and/or other impurities). For example, the water may be processed or unprocessed prior to step 1). Examples of processes that may be used for purifying the water include distilling, filtering, deionizing, and combinations of two or more thereof, such that the water may be deionized, distilled, and/or filtered. Alternatively, the water may be unprocessed (e.g. may be tap water, i.e., provided by a municipal water system or well water, used without further purification).

The water may be added in one or more aliquots in different process steps, which will be selected by one of skill in the art, depending on various factors, e.g., case of mixing and ease of adding other starting materials to the emulsion.

The total amount of water may be 25 weight parts to 75 weight parts, alternatively 30 weight parts to 70 weight parts, alternatively 35 weight parts to 65 weight parts, alternatively 40 weight parts to 60 weight parts, alternatively 45 weight parts to 55 weight parts, and alternatively 50 weight parts. Alternatively, the total amount of water in the emulsion may be 25 weight parts to 50 weight parts, alternatively 30 weight parts to <50 weight parts, alternatively 35 weight parts to 45 weight parts, and alternatively 35 weight parts to 40 weight parts.

D) Salt

Starting material D) in the emulsion prepared as described herein is a salt. A salt is a molecule with positive and negative ions that are held together by the strong attraction of particles with opposite charges. A salt is water soluble, if it dissolves in water to give a solution where the ions disperse at RT. A salt is insoluble, if the concentration of an aqueous solution is less than 0.001 M at room temperature; insoluble salts are not used herein. Examples of water soluble salts suitable for use as starting material D) are as described in Solubility (purdue.edu) and shown below in Table 1.

TABLE 1

| Soluble Salts |
| --- |
| 1. The $Na^+$, $K^+$, and $NH_4^+$ ions form soluble salts. Thus, NaCl, $KNO_3$, $(NH_4)_2SO_4$, $Na_2S$, and $(NH_4)_2CO_3$ are soluble. |
| 2. The nitrate ($NO_3^-$) ion forms soluble salts. Thus, $Cu(NO_3)_2$ and $Fe(NO_3)_3$ are soluble. |
| 3. The chloride ($Cl^-$), bromide ($Br^-$), and iodide ($I^-$) ions generally form soluble salts. Exceptions to this rule include salts of the $Pb^{2+}$, $Hg_2^{2+}$, $Ag^+$, and $Cu^+$ ions. $ZnCl_2$ is soluble, but CuBr is not. |
| 4. The sulfate ($SO_4^{2-}$) ion generally forms soluble salts. Exceptions include $BaSO_4$, $SrSO_4$, and $PbSO_4$, which are insoluble, and $Ag_2SO_4$, $CaSO_4$, and $Hg_2SO_4$, which are slightly soluble. |
| 5. Sulfides ($S^{2-}$) are usually insoluble. Exceptions include $Na_2S$, $K_2S$, $(NH_4)_2S$, MgS, CaS, SrS, and BaS, which are soluble. |
| 6. Oxides ($O^{2-}$) are usually insoluble. Exceptions include $Na_2O$, $K_2O$, SrO, and BaO, which are soluble, and CaO, which is slightly soluble. |
| 7. Hydroxides ($OH^-$) are usually insoluble. Exceptions include NaOH, KOH, $Sr(OH)_2$, and $Ba(OH)_2$, which are soluble, and $Ca(OH)_2$, which is slightly soluble. |
| 8. Chromates ($CrO_4^{2-}$) are usually insoluble. Exceptions include $Na_2CrO_4$, $K_2CrO_4$, $(NH_4)_2CrO_4$, and $MgCrO_4$, which are soluble. |
| 9. Phosphates ($PO_4^{3-}$) and carbonates ($CO_3^{2-}$) are usually insoluble. Exceptions include salts of the $Na^+$, $K^+$, and $NH_4^+$ ions, which are soluble. |

Alternatively, the soluble salt selected for starting material D) may have formula $MR^5_x$, where M is selected from the group consisting of Calcium (Ca), Magnesium (Mg), Potassium (K), Ammonium ($NH_4$), and Sodium (Na); $R^5$ is selected from the group consisting of a halogen atom, acetate group, a benzoate group, and a sulfate group; and subscript x is 1 or 2. Alternatively, the halogen atom may be selected from the group consisting of bromine (Br), chlorine (Cl), and iodine (I). Alternatively, D) the water soluble salt may be selected from the group consisting of ammonium chloride, calcium bromide, calcium chloride, calcium iodide, calcium sulfate, magnesium chloride, potassium bromide, potassium chloride, sodium acetate, sodium benzoate, sodium bromide, sodium chloride, sodium iodide, and a combination of two or more thereof. Alternatively, D) the water soluble salt may comprise sodium benzoate and one or more of ammonium chloride, calcium bromide, calcium chloride, calcium iodide, calcium sulfate, magnesium chloride, potassium bromide, potassium chloride, sodium acetate, sodium bromide, sodium chloride, and sodium iodide. The salts above are commercially available from various sources. Without wishing to be bound by theory, it is thought that $Ca_3(PO_4)_2$ is not suitable for use as the salt herein due to its insufficient solubility in water for this application.

The amount of D) the salt is sufficient to provide the beneficial viscosity effect described below. The amount of the salt may be 0.02 weight part to 1 weight part, alternatively 0.025 to 0.8 weight part, alternatively 0.03 to 0.6 weight part, alternatively 0.035 to 0.5 weight part, alternatively 0.04 to 0.4 weight part, alternatively 0.045 to 0.3 weight part, alternatively 0.05 to 0.2 weight part, alternatively 0.055 to 0.1 weight part, alternatively 0.06 weight part.

E) pH Adjusting Agent

Starting material E) in the emulsion prepared as described herein is a pH adjusting agent. Suitable pH adjusting agents can be any acid or base that does not react with A) the amino-functional polyorganosiloxane. Suitable acids include acetic acid, maleic acid, or lactic acid. Suitable bases include a tertiary amine, e.g., triethanolamine. Acids and bases suitable as pH adjusting agents are known in the art and are commercially available. The amount of pH adjusting agent depends on various factors such as how C) the water is processed before use and any impurities in the water, however, the amount of pH adjusting agent may be 0.02 weight part to 0.2 weight part, alternatively 0.03 weight part to 0.19 weight part, alternatively 0.04 weight part to 0.18 weight part, alternatively 0.05 weight part to 0.17 weight part, alternatively 0.06 weight part to 0.16 weight part, alternatively 0.07 weight part to 0.15 weight part, alternatively 0.08 weight part to 0.14 weight part, alternatively 0.09 weight part to 0.13 weight part, alternatively 0.1 weight part to 0.12 weight part, and alternatively 0.12 weight part.

F) Preservative

Starting material F) is a preservative added to the emulsion to impede microbial growth. The preservative may be —OH functional. Representative preservatives, which can be used include phenoxyethanol, ethylhexylglycerin, benzyl alcohol, caprylyl glycol, chlorphenesin, and a combination of two or more thereof. These preservatives are commercially available from various sources, such as the MICROCARE™ products, which are ECOCERT compliant, Phenoxyethanol & blends, and Others available from THOR Especialidades, S.A. of Barcelona, Spain on the website at Preservatives-THOR Personal Care-Microcare. The exact amount of preservative depends on various factors including the selection of the preservative and the other starting materials used to make the emulsion. However, the amount of preservative may be 0.3 weight part to 2 weight parts, alternatively 0.5 weight part to 1.9 weight parts, alternatively 0.75 weight part to 1.8 weight parts, alternatively 1 weight part to 1.7 weight parts, alternatively 1.5 weight parts to 1.6 weight parts.

Adding D) the salt to the emulsion in the process described herein can cause a significant and surprising drop in bulk viscosity. Without wishing to be bound by theory, it is thought that the combination of A) the amino-functional polyorganosiloxane, B) the non-ionic surfactant, and —OH functional preservative (e.g., phenoxyethanol and benzyl alcohol) can cause the formation of large emulsion particles, which are believed to cause a significant increase in bulk viscosity, which is undesirable. In the past, additional water may have been added to reduce viscosity. Without wishing to be bound by theory, D) the salt is believed to destabilize the large emulsion particles to release water and thereby lower viscosity of the resulting emulsion. The inventors surprisingly found that even at relatively low amounts of water in the emulsion produced as described herein, the viscosity remained low enough that the emulsion was flowable at room temperature, and the emulsion was stable with time (e.g., no significant increase in viscosity that would render the emulsion unflowable or separation of the components of the emulsion was observed after 30 days at 50° C., in contrast, the inventors surprisingly found that storage under these conditions contributed to viscosity reduction of the emulsion). It is thought that the ions formed by dissolving the salt produce viscosity decrease (thinning effect) in the emulsion prepared as described herein. The flowable nature of the product of step 2) allows for easy incorporation of the remaining starting materials E), F), and when present G), which offers energy savings and capacity increases in the manufacturing facility. The lower viscosity also allows for easy filtration and packaging of the emulsion produced when the process is complete. The customer benefits from an easier to incorporate emulsion into the end use formulation.

Optional G) Freeze Inhibitor

Starting material G) in the emulsion is an optional freeze inhibitor. Suitable freeze inhibitors additives are known in the art and are commercially available. The freeze inhibitor can be a glycol, such as propylene glycol, ethylene glycol, or a combination thereof. The amount of the freeze inhibitor may be 0 to 2, alternatively 0.1 to 1.75, alternatively 0.2 to 1.5, alternatively 0.3 to 1.25, alternatively 0.4 to 1, and alternatively 0.5 weight part.

When selecting starting materials for the emulsion, there may be overlap between types of starting materials because certain starting materials described herein may have more than one function. For example, certain glycols may be useful as freeze inhibitors and as preservatives. When adding starting materials during the process to form the emulsion, the starting materials are distinct from one another.

The process described herein produces an emulsion, which is an oil-in-water emulsion. Said emulsion can be produced with different particle sizes by adjusting the amount of shear applied and the amount of water utilized in step 1). Particle sizes diameters determined by volume with 50% of cumulative population may vary from 0.18 microns to 10 microns in size. Alternatively, particle sizes of 0.25 micron to 0.75 micron may be produced and may be desirable to maintain stability against destabilization in the form of creaming. Particle size may be determined by laser diffraction using a Malvern Mastersizer 3000 and in accordance ISO 13320 (2009).

Method of Use

Amino-functional polyorganosiloxanes are useful in the textile industry as fiber lubricants, for example for polyester, polyamide, acrylic, cotton or wool fibers; as fabric softeners; and as anti-wrinkle agents. Amino-functional polyorganosiloxanes are also useful in the personal care industry, for example, in hair care compositions such as shampoos, conditioners, and styling products, and also in skin care compositions such as cosmetic compositions. The emulsion prepared as described above may be used to deliver the amino-functional polyorganosiloxane in one or more of the above applications. For example, the emulsion prepared as described herein may be used in addition to, or instead of, any of the emulsions described, for example, in U.S. Pat. No. 7,781,505 to Cook, et al.; U.S. Patent Application Publication 2018/0353396 to Paul, et al.; U.S. Patent Application, Publication 2022/0008320 to Liang, et al., and U.S. Pat. No. 6,171,515 to Evans et al. Therefore, a method comprises using the emulsion described above in a hair care composition. For example, the method may comprise applying to hair, the emulsion, or a hair care composition comprising the emulsion. Alternatively, a method for treating textiles comprises applying to the textile the emulsion prepared as described above, or a textile treatment agent comprising the emulsion.

EXAMPLES

These examples are intended to illustrate the invention to one of ordinary skilled in the art and should not be construed as limiting the scope of the invention set forth in the claims. All measurements and experiments were conducted at 23° C., unless indicated otherwise.

Example 1—Preparation of Emulsion A

To a 3 L stainless steel beaker was added 500.00 g of amino-functional polyorganosiloxane, 5.65 g of TERGITOL™ 15-S-7, 37.50 g of TERGITOL™ 15-S-12. The beaker and contents were placed under an overhead benchtop mixer with a shaft containing a three blade propeller directly above a propeller of six 90° blades. The contents were mixed at 150 rpm for 5 minutes or until they were homogeneous. The mixer was stopped, and 75.00 g of water was added. Mixing continued at 700 rpm for 5 minutes. After 5 minutes, the mixer was stopped, phase inversion of the contents of the beaker was observed followed by confirmation through particle size analysis on the Malvern Mastersizer 3000. The emulsion was scraped from the side walls and blades with a rubber spatula and mixing continued for an additional 15 minutes at 350 rpm. Particle size was measured again. Dilution of the emulsion occurred in two increments totaling 354.85 g of water with mixing occurring at 350 rpm and 150 rpm respectively for 10 minutes each. A 20% acetic acid solution, phenoxyethanol, benzyl alcohol and propylene glycol were all added in separately with 10 minutes of mixing between each of these starting materials. The mixer was stopped occasionally and scraped to ensure full incorporation of starting materials into the emulsion at each step. After mixing was completed and ensured to be homogeneous, the emulsion was collected. Visual observations, viscosity and particle size were recorded. Viscosity was measured using a Brookfield DV II Viscometer Spindle #4 at 0.5 rpm.

Example 2—Preparation of Emulsion B

In a 1 oz. glass vial was added 1 g of water with 0.03 g of sodium benzoate. This vial was vortexed to ensure that the sodium benzoate salt dissolved, creating a transparent solution. To a 60 g Speedmixer dental mixer cup was added 48.94 g of Emulsion A from Example 1 and the sodium benzoate solution. The dental mixer cup contents were sheared on a Hauschild Speedmixer (Model DAC 150 FVZ) for 30 seconds at 3500 rpm. The cup was scraped with a spatula, and the contents were mixed for an additional 30 seconds at 3500 rpm. Visual observations, viscosity and particle size were recorded. Viscosity was measured using a Brookfield DV II Viscometer Spindle #3 at 60 rpm.

Example 3—Preparation of Emulsion C

In a 1 oz. glass vial was added 1 g of water with 0.03 g of sodium chloride. This vial was vortexed to ensure that the sodium chloride salt dissolved, creating a transparent solution. To a 60 g Speedmixer dental mixer cup was added 48.94 g of Emulsion A from Example 1 and the sodium chloride solution. The dental mixer cup contents were sheared on a Hauschild Speedmixer (Model DAC 150 FVZ) for 30 seconds at 3500 rpm. The cup was scraped with a spatula, and the contents were mixed for an additional 30 seconds at 3500 rpm. Visual observations, viscosity and particle size were recorded. Viscosity was measured using a Brookfield DV II Viscometer Spindle #3 at 60 rpm.

Example 4—Preparation of Emulsion D

In a 1 oz. glass vial was added 1 g of water with 0.03 g of sodium bromide. This vial was vortexed to ensure that the sodium bromide salt dissolved, creating a transparent solution. To a 60 g Speedmixer dental mixer cup was added 48.94 g of Emulsion A from Example 1 and the sodium bromide solution. The dental mixer cup contents were sheared on a Hauschild Speedmixer (Model DAC 150 FVZ) for 30 seconds at 3500 rpm. The cup was scraped with a spatula, and the contents were mixed for an additional 30 seconds at 3500 rpm. Visual observations, viscosity and particle size were recorded. Viscosity was measured using a Brookfield DV II Viscometer Spindle #3 at 60 rpm.

Example 5—Preparation of Emulsion E

In a 1 oz. glass vial was added 1 g of water with 0.03 g of sodium acetate. This vial was vortexed to ensure that the sodium acetate salt dissolved, creating a transparent solution. To a 60 g Speedmixer dental mixer cup was added 48.94 g of Emulsion A from Example 1 and the sodium acetate solution. The dental mixer cup contents were sheared on a Hauschild Speedmixer (Model DAC 150 FVZ) for 30 seconds at 3500 rpm. The cup was scraped with a spatula, and the contents were mixed for an additional 30 seconds at 3500 rpm. Visual observations, viscosity and particle size were recorded. Viscosity was measured using a Brookfield DV II Viscometer Spindle #3 at 60 rpm.

Example 6—Preparation of Emulsion F

In a 1 oz. glass vial was added 1 g of water with 0.03 g of sodium iodide. This vial was vortexed to ensure that the sodium iodide salt dissolved, creating a transparent solution. To a 60 g Speedmixer dental mixer cup was added 48.94 g of Emulsion A from Example 1 and the sodium iodide solution. The dental mixer cup contents were sheared on a Hauschild Speedmixer (Model DAC 150 FVZ) for 30 seconds at 3500 rpm. The cup was scraped with a spatula, and the contents were mixed for an additional 30 seconds at 3500 rpm. Visual observations, viscosity and particle size were recorded. Viscosity was measured using a Brookfield DV II Viscometer Spindle #3 at 60 rpm.

Example 7—Preparation of Emulsion G

In a 1 oz. glass vial was added 1 g of water with 0.03 g of calcium chloride. This vial was vortexed to ensure that the calcium chloride salt dissolved, creating a transparent solution. To a 60 g Speedmixer dental mixer cup was added 48.94 g of Emulsion A from Example 1 and the calcium chloride solution. The dental mixer cup contents were sheared on a Hauschild Speedmixer (Model DAC 150 FVZ) for 30 seconds at 3500 rpm. The cup was scraped with a spatula, and the contents were mixed for an additional 30 seconds at 3500 rpm. Visual observations, viscosity and particle size were recorded. Viscosity was measured using a Brookfield DV II Viscometer Spindle #3 at 60 rpm.

Example 8—Preparation of Emulsion H

In a 1 oz. glass vial was added 1 g of water with 0.03 g of calcium bromide. This vial was vortexed to ensure that the calcium bromide salt dissolved, creating a transparent solution. To a 60 g Speedmixer dental mixer cup was added 48.94 g of Emulsion A from Example 1 and the calcium bromide solution. The dental mixer cup was sheared on a Hauschild Speedmixer (Model DAC 150 FVZ) for 30 seconds at 3500 rpm. The cup was scraped with a spatula, and the contents were mixed for an additional 30 seconds at 3500 rpm. Visual observations, viscosity and particle size were recorded. Viscosity was measured using a Brookfield DV II Viscometer Spindle #3 at 60 rpm.

Example 9—Preparation of Emulsion I

In a 1 oz. glass vial was added 1 g of water with 0.03 g of calcium sulfate. This vial was vortexed to ensure that the calcium sulfate salt dissolved creating a transparent solution. To a 60 g Speedmixer dental mixer cup was added 48.94 g of Emulsion A from Example 1 and the calcium sulfate solution. The dental mixer cup contents were sheared on a Hauschild Speedmixer (Model DAC 150 FVZ) for 30 seconds at 3500 rpm. The cup was scraped with a spatula, and the contents were mixed for an additional 30 seconds at 3500 rpm. Visual observations, viscosity and particle size were recorded. Viscosity was measured using a Brookfield DV II Viscometer Spindle #3 at 60 rpm.

Example 10—Preparation of Emulsion J

In a 1 oz. glass vial was added 1 g of water with 0.03 g of calcium iodide. This vial was vortexed to ensure that the calcium iodide salt dissolved, creating a transparent solution. To a 60 g Speedmixer dental mixer cup was added 48.94 g of Emulsion A from Example 1 and the calcium iodide solution. The dental mixer cup contents were sheared on a Hauschild Speedmixer (Model DAC 150 FVZ) for 30 seconds at 3500 rpm. The cup was scraped with a spatula, and the contents were mixed for an additional 30 seconds at 3500 rpm. Visual observations, viscosity and particle size were recorded. Viscosity was measured using a Brookfield DV II Viscometer Spindle #3 at 60 rpm.

Example 11—Preparation of Emulsion K

In a 1 oz. glass vial was added 1 g of water with 0.03 g of ammonium chloride. This vial was vortexed to ensure that the ammonium chloride salt dissolved, creating a transparent solution. To a 60 g Speedmixer dental mixer cup was added 48.94 g of Emulsion A from Example 1 and the ammonium chloride solution. The dental mixer cup contents were sheared on a Hauschild Speedmixer (Model DAC 150 FVZ) for 30 seconds at 3500 rpm. The cup was scraped with a spatula, and the contents were mixed for an additional 30 seconds at 3500 rpm. Visual observations, viscosity and particle size were recorded. Viscosity was measured using a Brookfield DV II Viscometer Spindle #3 at 60 rpm.

Example 12—Preparation of Emulsion L

In a 1 oz. glass vial was added 1 g of water with 0.03 g of potassium chloride. This vial was vortexed to ensure that the potassium chloride salt dissolved, creating a transparent solution. To a 60 g Speedmixer dental mixer cup was added 48.94 g of Emulsion A from Example 1 and the potassium chloride solution. The dental mixer cup contents were sheared on a Hauschild Speedmixer (Model DAC 150 FVZ) for 30 seconds at 3500 rpm. The cup was scraped with a spatula, and the contents were mixed for an additional 30 seconds at 3500 rpm. Visual observations, viscosity and particle size were recorded. Viscosity was measured using a Brookfield DV II Viscometer Spindle #3 at 60 rpm.

Example 13—Preparation of Emulsion M

In a 1 oz. glass vial was added 1 g of water with 0.03 g of potassium bromide. This vial was vortexed to ensure that the potassium bromide salt dissolved, creating a transparent solution. To a 60 g Speedmixer dental mixer cup was added 48.94 g of Emulsion A from Example 1 and the potassium bromide solution. The dental mixer cup contents were sheared on a Hauschild Speedmixer (Model DAC 150 FVZ) for 30 seconds at 3500 rpm. The cup was scraped with a spatula, and the contents were mixed for an additional 30 seconds at 3500 rpm. Visual observations, viscosity and particle size were recorded. Viscosity was measured using a Brookfield DV II Viscometer Spindle #3 at 60 rpm.

Example 14—Preparation of Emulsion N

In a 1 oz. glass vial was added 1 g of water with 0.03 g of magnesium chloride. This vial was vortexed to ensure that the magnesium chloride salt dissolved, creating a transparent solution. To a 60 g Speedmixer dental mixer cup was added 48.94 g of Emulsion A from Example 1 and the magnesium chloride solution. The dental mixer cup contents were sheared on a Hauschild Speedmixer (Model DAC 150 FVZ) for 30 seconds at 3500 rpm. The cup was scraped with a spatula, and the contents were mixed for an additional 30 seconds at 3500 rpm. Visual observations, viscosity and particle size were recorded. Viscosity was measured using a Brookfield DV II Viscometer Spindle #3 at 60 rpm.

Example 15—Preparation of Emulsion O

In a 1 oz. glass vial was added 1 g of water with 0.03 g of calcium phosphate. This vial was vortexed, and the solution was noted to be cloudy. To a 60 g Speedmixer dental mixer cup was added 48.94 g of Emulsion A from Example 1 and the calcium phosphate solution. The dental mixer cup contents were sheared on a Hauschild Speedmixer (Model DAC 150 FVZ) for 30 seconds at 3500 rpm. The cup was scraped with a spatula, and the contents were mixed for an additional 30 seconds at 3500 rpm. Visual observations, viscosity and particle size were recorded. Viscosity was measured using a Brookfield DV II Viscometer Spindle #4 at 0.5 rpm.

The starting materials used to prepare the emulsions in Examples 1 to 18 are described below. The amino-functional polyorganosiloxane was DOWSIL™ AP 6087 Fluid, the non-ionic surfactant was a mixture of TERGITOL™ 15-S-7 and TERGITOL™ 15-S-12, the acetic acid (from Haviland), Phenoxyethanol (from Clariant), Benzyl Alcohol (from Univar), and Propylene glycol (The Dow Chemical Company).

Table 1 shows the salts used in Examples 2 through 15

| Emulsion ID | Salt | Water solubility at 25° C. | Vendor |
|---|---|---|---|
| A, P, Q, R | N/A | N/A | N/A |
| B | Na Benzoate | soluble | Fisher |
| C | NaCl | soluble | Sigma-Aldrich |
| D | NaBr | soluble | Sigma-Aldrich |
| E | NaOAc | soluble | Alfa Aesar |
| F | NaI | soluble | Sigma-Aldrich |
| G | $CaCl_2$ | soluble | Alfa Aesar |
| H | $CaBr_2$ | soluble | Alfa Aesar |
| I | $CaSO_4$ | soluble | Sigma-Aldrich |
| J | $CaI_2$ | soluble | Alfa Aesar |
| K | $NH_4Cl$ | soluble | Alfa Aesar |
| L | KCl | soluble | Fisher |
| M | KBr | soluble | Alfa Aesar |
| N | MgCl | soluble | Acros |
| O | $Ca_3(PO_4)_2$ | insoluble | Alfa Aesar |

Table 2 shows the weight % make up of each emulsion above.

| Emulsion ID | A | B | C | D | E | F | G | H |
|---|---|---|---|---|---|---|---|---|
| Example # | 1 | 2 | 3 | 4 | 5 | 6 | 7 | 8 |
| AP 6087 Fluid | 50.00 | 50.00 | 50.00 | 50.00 | 50.00 | 50.00 | 50.00 | 50.00 |
| Tergitol 15-S-7 | 0.57 | 0.57 | 0.57 | 0.57 | 0.57 | 0.57 | 0.57 | 0.57 |
| Tergitol 15-S-12 | 3.76 | 3.76 | 3.76 | 3.76 | 3.76 | 3.76 | 3.76 | 3.76 |
| Water | q.s. to 100 | q.s.* to 100 | q.s. to 100 | q.s. to 100 | q.s. to 100 | q.s. to 100 | q.s. to 100 | q.s. to 100 |
| Sodium Benzoate | 0 | 0.06 | 0 | 0 | 0 | 0 | 0 | 0 |
| NaCl | 0 | 0 | 0.06 | 0 | 0 | 0 | 0 | 0 |
| NaBr | 0 | 0 | 0 | 0.06 | 0 | 0 | 0 | 0 |
| NaOAc | 0 | 0 | 0 | 0 | 0.06 | 0 | 0 | 0 |
| NaI | 0 | 0 | 0 | 0 | 0 | 0.06 | 0 | 0 |

-continued

| | | | | | | | | |
|---|---|---|---|---|---|---|---|---|
| $CaCl_2$ | 0 | 0 | 0 | 0 | 0 | 0 | 0.06 | 0 |
| $CaBr_2$ | 0 | 0 | 0 | 0 | 0 | 0 | 0 | 0.06 |
| Acetic Acid (20%) | 0.60 | 0.60 | 0.60 | 0.60 | 0.60 | 0.60 | 0.60 | 0.60 |
| Phenoxy-ethanol | 0.90 | 0.90 | 0.90 | 0.90 | 0.90 | 0.90 | 0.90 | 0.90 |
| Benzyl Alcohol | 0.70 | 0.70 | 0.70 | 0.70 | 0.70 | 0.70 | 0.70 | 0.70 |
| Propylene Glycol | 0.50 | 0.50 | 0.50 | 0.50 | 0.50 | 0.50 | 0.50 | 0.50 |

| Emulsion ID | I | J | K | L | M | N | O |
|---|---|---|---|---|---|---|---|
| Example # | 9 | 10 | 11 | 12 | 13 | 14 | 15 |
| AP 6087 Fluid | 50.00 | 50.00 | 50.00 | 50.00 | 50.00 | 50.00 | 50.00 |
| Tergitol 15-S-7 | 0.57 | 0.57 | 0.57 | 0.57 | 0.57 | 0.57 | 0.57 |
| Tergitol 15-S-12 | 3.76 | 3.76 | 3.76 | 3.76 | 3.76 | 3.76 | 3.76 |
| Water | q.s. to 100 | q.s. to 100 | q.s. to 100 | q.s. to 100 | q.s. to 100 | q.s. to 100 | q.s. to 100 |
| $CaSO_4$ | 0.06 | 0 | 0 | 0 | 0 | 0 | 0 |
| $CaI_2$ | 0 | 0.06 | 0 | 0 | 0 | 0 | 0 |
| $NH_4Cl$ | 0 | 0 | 0.06 | 0 | 0 | 0 | 0 |
| KCl | 0 | 0 | 0 | 0.06 | 0 | 0 | 0 |
| KBr | 0 | 0 | 0 | 0 | 0.06 | 0 | 0 |
| MgCl | 0 | 0 | 0 | 0 | 0 | 0.06 | 0 |
| $Ca_3(PO_4)_2$ | 0 | 0 | 0 | 0 | 0 | 0 | 0.06 |
| Acetic Acid (20%) | 0.60 | 0.60 | 0.60 | 0.60 | 0.60 | 0.60 | 0.60 |
| Phenoxy-ethanol | 0.90 | 0.90 | 0.90 | 0.90 | 0.90 | 0.90 | 0.90 |
| Benzyl Alcohol | 0.70 | 0.70 | 0.70 | 0.70 | 0.70 | 0.70 | 0.70 |
| Propylene Glycol | 0.50 | 0.50 | 0.50 | 0.50 | 0.50 | 0.50 | 0.50 |

*q.s = quantum satis

Table 3 shows the particle size as measured by the Malvern Mastersizer 3000, viscosity as measured by the Brookfield DV II Viscometer with varying spindles, and visual observations for each example.

| Emulsion ID | Salt | D(v, 0.1) um | D(v, 0.5) um | D(v, 0.9) um | Viscosity (cP) | DV II Spindle # | Visual observation |
|---|---|---|---|---|---|---|---|
| A | Control no salt | 0.224 | 0.516 | 1.07 | 53717 | 4 | not flowable |
| B | Sodium Benzoate | 0.0945 | 0.289 | 0.92 | 1560 | 3 | flowable |
| C | NaCl | 0.0939 | 0.307 | 0.97 | 1300 | 3 | flowable |
| D | NaBr | 0.0796 | 0.281 | 0.895 | 1320 | 3 | flowable |
| E | NaOAc | 0.0957 | 0.331 | 1.22 | 3205 | 3 | flowable |
| F | NaI | 0.0905 | 0.307 | 0.979 | 2780 | 3 | flowable |
| G | $CaCl_2$ | 0.0916 | 0.306 | 0.942 | 1270 | 3 | flowable |
| H | $CaBr_2$ | 0.0845 | 0.302 | 1.01 | 2560 | 3 | flowable |
| I | $CaSO_4$ | 0.0733 | 0.275 | 0.923 | 2751 | 3 | flowable |
| J | $CaI_2$ | 0.0941 | 0.335 | 3.9 | 2640 | 3 | flowable |
| K | $NH_4Cl$ | 0.0834 | 0.287 | 0.914 | 3305 | 3 | flowable |
| L | KCl | 0.0878 | 0.294 | 0.916 | 2505 | 3 | flowable |
| M | KBr | 0.072 | 0.259 | 0.899 | 1340 | 3 | flowable |
| N | MgCl | 0.0899 | 0.303 | 0.944 | 1290 | 3 | flowable |
| O | $Ca_3(PO_4)_2$ | 0.105 | 0.368 | 1.72 | 53210 | 4 | not flowable |

Problem to be Addressed

An aqueous emulsion of an amino-functional polyorganosiloxane containing a non-ionic surfactant package was produced using a preservative package that was discovered to increase viscosity. The emulsion was found to be no longer flowable. The increased viscosity was only partially mitigated by reducing the content of the amino-functional polyorganosiloxane from 50% down to 37.5% and having 50% or less of amino-functional polyorganosiloxane in the emulsion may be undesirable to some customers. Attempts to hasten the thinning by adding a heating step during the process was not effective in a reasonable manufacturing time frame.

Solution

The process described herein produces an emulsion with viscosity and particle size that are stable, even after storage of the emulsion for 6 months at RT, or 30 days at 50° C. The emulsion also can withstand freeze conditions. The process allows for production of an emulsion with relatively high amino-functional polyorganosiloxane content and relatively low water content.

Definitions and Usage of Terms

All amounts, ratios, and percentages are by weight unless otherwise indicated. The articles ‘a’, ‘an’, and ‘the’ each refer to one or more, unless otherwise indicated. The disclosure of ranges includes the range itself and also anything subsumed therein, as well as endpoints. Similarly, the disclosure of Markush groups includes the entire group and also any individual members and subgroups subsumed therein. For example, disclosure of the Markush group methyl, ethyl, propyl, and butyl includes the member ethyl individually; the subgroup methyl and ethyl; and any other individual member and subgroup subsumed therein.

Abbreviations used herein are defined as follows. The abbreviation "cP" means centiPoise. The abbreviation "g" means gram. "L" means liter. The abbreviation "oz" means ounce. The abbreviation "rpm" means revolutions per minute. "RT" means room temperature of 23° C.±2° C.

The invention claimed is:

1. A process for preparing an emulsion, wherein the process comprises:

1) mixing starting materials comprising
 25 weight parts to 75 weight parts of A) an amino-functional polyorganosiloxane;
 2 weight parts to 10 weight parts of B) a non-ionic surfactant; and
 4 weight parts to 20 weight parts of C) water;
2) mixing, with the product of step 1), a starting material comprising
 0.02 weight parts to 1 weight parts of D) a water soluble salt, thereby reducing bulk viscosity of the emulsion, and
 additional water; and
3) mixing starting materials comprising
 E) a pH adjusting agent,
 F) a preservative, and
 optionally G) a freeze inhibitor;
 with the proviso that the emulsion is free of cationic surfactants.

2. The process of claim 1, where starting material A) comprises a poly(dialkyl/alkylamino) siloxane of unit formula $(R^1{}_2SiO_{2/2})_a(R^1R^2SiO_{2/2})_b(ZO_{1/2})_d(R^1{}_3SiO_{1/2})_e$, where each $R^1$ is an independently selected alkyl group of 1 to 6 carbon atoms; each $R_2$ is an independently selected amino-functional alkyl group of formula $ZHN—R^3—(ZNR^4)_c—$, where $R^3$ is an alkylene group of 2 to 6 carbon atoms, $R^4$ is an alkylene group of 2 to 6 carbon atoms, and subscript c is 0 or 1; each Z is independently selected from the group consisting of H and $R^1$; subscripts a, b, d, and e represent average number, per molecule, of each unit in the unit formula, subscript a is 1 to 5, subscript b is 1 to 1000, subscript d is 0, 1 or 2; subscript e is 0, 1, or 2; and a quantity (d+e)=2.

3. The process of claim 1, where B) the non-ionic surfactant comprises a secondary alcohol ethoxylate.

4. The process of claim 1, where step 1) is performed at: a temperature of 10° C. to 70° C., a shear rate of 70 $s^{-1}$ to 700 $s^{-1}$, and a pressure of 100 torr to 760 torr.

5. The process of claim 1, where step 1) comprises first mixing A) the amino-functional polyorganosiloxane and B) the non-ionic surfactant; and thereafter mixing C) the water with the mixture of A) and B).

6. The process of claim 1, where D) the salt has formula $MR^5{}_x$, where M is selected from the group consisting of Calcium (Ca), Magnesium (Mg), Potassium (K), Ammonium ($NH_4$), and Sodium (Na); $R^5$ is selected from the group consisting of a halogen atom, acetate group, a benzoate group, and a sulfate group; and subscript x is 1 or 2.

7. The process of claim 6, where the halogen atom is selected from the group consisting of Br, Cl, and I.

8. The process of claim 6, where D) the salt is selected from the group consisting of ammonium chloride, calcium bromide, calcium chloride, calcium iodide, calcium sulfate, magnesium chloride, potassium bromide, potassium chloride, sodium acetate, sodium benzoate, sodium bromide, sodium chloride, sodium iodide, and a combination of two or more thereof.

9. The process of claim 8, where D) the salt comprises sodium benzoate and one or more of ammonium chloride, calcium bromide, calcium chloride, calcium iodide, calcium sulfate, magnesium chloride, potassium bromide, potassium chloride, sodium acetate, sodium bromide, sodium chloride, and sodium iodide.

10. The process of claim 1, where step 2) and step 3) are performed at: a temperature of 10° C.-70° C., a shear rate of 7 $s^{-1}$-90 $s^{-1}$, and a pressure of 100 torr-760 torr.

11. The process of claim 1, further comprising one or more additional steps selected from:
 adding additional water after step 1) and before step 2) and mixing;
 adding additional water during or after step 2) and before step 3) and mixing; and
 adding additional water during or after step 3) and mixing.

12. The process of claim 1, where E) the pH adjusting agent comprises acetic acid.

13. The process of claim 1, where F) the preservative comprises phenoxy ethanol, benzyl alcohol or a combination thereof.

14. The process of claim 1, where G), the freeze inhibitor is present, and where the freeze inhibitor is selected from the group consisting of propylene glycol, ethylene glycol, and a combination thereof.

15. An emulsion prepared by the process of claim 1, wherein the emulsion comprises:
 25-75 weight parts of A) the amino-functional polyorganosiloxane,
 2-10 weight parts of B) the non-ionic surfactant,
 25-75 weight parts of C) water,
 0.02-1 weight part of D) the salt,
 0.02-0.2 weight part of E) the pH adjusting agent,
 0.3-2 weight part of F) the preservative, and
 0-2 weight part of G) the freeze inhibitor.

16. The process of claim 1, wherein the emulsion consists essentially of starting materials A), B), C), D), E), F), and G).

17. The process of claim 16, wherein the emulsion consists of starting materials A), B), C), D), E), F), and G).

* * * * *